United States Patent
Harwood

(10) Patent No.: US 6,861,049 B2
(45) Date of Patent: Mar. 1, 2005

(54) AQUEOUS SLURRIES USEFUL FOR CLEANING THE TONGUE AND THROAT

(76) Inventor: Douglas B. Harwood, 5614 Cape George Rd., Port Townsend, WA (US) 98368

( * ) Notice: Subject to any disclaimer, the term of this patent is extended or adjusted under 35 U.S.C. 154(b) by 0 days.

(21) Appl. No.: 10/293,813

(22) Filed: Nov. 12, 2002

(65) Prior Publication Data

US 2004/0091430 A1 May 13, 2004

(51) Int. Cl.$^7$ .......................... A61K 33/44; A61K 7/16; A01N 59/00
(52) U.S. Cl. .......................... 424/49; 424/125; 433/216
(58) Field of Search .................... 424/49, 125; 433/216

(56) References Cited

U.S. PATENT DOCUMENTS 6,685,474 B2 * 2/2004 Harwood ................. 433/217.1

OTHER PUBLICATIONS

Makosiej et al., Journal of Toxicology. Clinical toxicology (1993) 31(3) 381–95 (abstract).*

* cited by examiner

*Primary Examiner*—Phyllis G. Spivack
(74) *Attorney, Agent, or Firm*—Seed IP Law Group PLLC

(57) ABSTRACT

Aqueous slurries for cleaning the tongue and throat comprising finely-divided charcoal, water and an alcohol biocide, optionally in the form of a kit, are disclosed.

19 Claims, No Drawings

AQUEOUS SLURRIES USEFUL FOR CLEANING THE TONGUE AND THROAT

BACKGROUND OF THE INVENTION

1. Field of the Invention

The present invention generally relates to compositions and methods useful for oral hygiene, and more particularly to compositions and methods that are useful for cleaning the tongue and throat of a warm-blooded animal, including a human.

2. Description of the Related Art

Practicing good oral hygiene is often directed to, for example, preventing tooth decay and periodontal disease (i.e., gum disease); preventing or mitigating halitosis (i.e., fetid breath); avoiding unsightly teeth, gums and tongue; and avoiding the onset of various illnesses and other diseases that may take hold in the mouth and throat. Practicing good oral hygiene largely amounts to thoroughly and assiduously removing from the mouth and throat various contaminants, including pathogens such as bacteria and viruses; food debris; and stains found therein.

Contaminants, such as bacteria and food matter may be found on all surfaces in the mouth. Areas that are particularly problematic in this regard include the areas between tooth enamel and gingival, or gum tissue (i.e., gingival crevices), interproximal tooth surfaces, the tongue, and the throat. Some of the bacteria is present in the form of a clear (almost invisible) sticky film having an organized structure and referred to as dental plaque ("plaque"), which adheres to tooth surfaces, gum tissues and the tongue. Plaque must be mechanically removed, and this is usually accomplished by brushing and flossing.

Despite normal diligence in removal of plaque, some amount of bacteria and plaque inevitably remains. In turn, calculus (also referred to as tartar) inevitably forms, thus, compounding the problem. It has been reported that 92% of Americans have a significant accumulation of calculus in their mouths. The result is tooth decay, periodontal disease and halitosis. It should also be noted that there are other deleterious consequences associated with the presence of viruses and bacteria in the mouth and throat. These include heart and blood vessel disease associated with bacteria entering the bloodstream and damaging heart muscle tissue and promoting blood clots, respiratory disease caused by bacteria ending up in airways, and colds and flues caused by viruses that take hold in mouth and throat areas.

Without question, a significant contributing factor in the above problem is the widespread belief, even by those who strive to practice good oral hygiene, that normal diligence in removing contaminants, such as food matter, bacteria and plaque, from the mouth amounts to thoroughly brushing teeth twice a day and proper flossing daily. Cleaning the tongue or throat is often omitted.

Yet, there appears to be ample evidence that effectively cleaning the tongue, for example, is an important component of oral hygiene. The filliform on the tongue surface readily capture food debris and bacteria. The captured food debris and normal mucous production yields a coating on the tongue surface. This, in turn, provides, particularly in the posterior area of the tongue dorsum, an aneorobic environment for various gram negative anaerobic bacteria, including: *A. actinomycetemcomitans, B. forsythus, T. denticola, P. intermedia,* and *P. gingivalis*. These bacteria are also found at the back of the throat, as are viruses.

Such bacteria are reported to be the primary source of gaseous volatile sulfur-bearing compounds that contribute to halitosis and the mineral-leaching acids that cause tooth decay. In one study, it was reported that the combination of tooth brushing and tongue cleaning reduced fetid breath by 85%, while the reduction realized by tongue cleaning alone was 75% and from tooth brushing alone was 25%. Further, such bacteria are a significant source of the plaque and calculus found on tooth surfaces and in gingival crevices, and associated periodontal disease. This is largely the result of their thriving in the anaerobic environment provided by the tongue, then swarming to those areas, thus, reducing the effectivity of extensive teeth and gum cleaning.

In summary, effective tongue and throat cleaning is beneficial in avoiding tooth decay and periodontal disease; fetid breath; heart, vessel and respiratory disease; as well as other illness and diseases that can take hold in the mouth, particularly in the throat. Other benefits of tongue cleaning include improving the appearance of the tongue (less coating) and of the teeth and gums (generally, less plaque and calculus resulting from contamination of the tongue); and improving the ability to taste and appreciate food by providing a cleaner palate.

Current methods for cleaning the tongue include brushing with a conventional toothbrush and toothpaste or water, typically while brushing teeth. Another method is to scrape the tongue surface. A number of plastic and metal tongue scrapers are commercially available. Yet another method is to rinse the mouth with a mouthrinse, alone or in combination with conventional brushing or scraping. Typically, throat cleaning is carried out by gargling or spraying the area with saltwater or a commercially-available mouthrinse.

The latter often may comprise alcohol and/or another bacteriostatic or bacteriocidal agent such as zinc gluconate, zinc chloride, triclosan, chlorine dioxide, or cetylpyridinium chloride (CPC). CPC is a quaternary ammonium compound that has demonstrated antimicrobial activity against a number of oral bacteria. Mouthrinses can act to clear the throat area of pathogens and debris by directly flushing away the same, by indirectly flushing away the same through stimulating the flow of saliva in the mouth, or by killing, and/or arresting the reproduction of, pathogens in the throat area. In addition, cleaning other areas of the oral cavity, as described previously, also helps to clean the throat.

The above-described methods are of limited effectiveness, however. Accordingly, there remains a need in the art for compositions and methods related thereto for cleaning the tongue and throat that are more effective than those currently used. The present invention fulfills these needs and provides further related advantages.

BRIEF SUMMARY OF THE INVENTION

In brief, the present invention, in one aspect, is directed to aqueous slurries useful for cleaning the tongue and throat of a warm-blooded animal, including a human ("patient"), to remove contaminants, such as pathogens and other debris, therefrom. Toward that end, the disclosed aqueous slurries are applied to surface areas of the tongue and throat in need thereof. In another aspect, the present invention is directed to methods for cleaning the tongue and throat of a patient. The methods comprise contacting areas thereof in need of cleaning with a disclosed aqueous slurry. The present invention, in yet another aspect, is directed to kits that provide readily used components for cleaning the tongue and throat of a patient by way of the disclosed methods and aqueous slurries.

More specifically, in one embodiment, the present invention is directed to aqueous slurries, useful for cleaning the tongue and throat of a patient, wherein the slurries are formed by combining finely-divided charcoal and a liquid portion, the latter comprising water and a biocide. Such slurries are effective in cleaning areas of the tongue and throat of a patient in need thereof.

In another aspect, the present invention is directed to methods for cleaning the tongue of a patient to at least reduce the contamination thereof. A representative method comprises: contacting an area of the tongue surface in need thereof with a disclosed aqueous slurry so as to contact contamination thereon for a period of time; removing at least a portion of the contacted contamination and used aqueous slurry from the area of the tongue surface; optionally, repeating the contacting and removing steps so as to effect a desired degree of cleaning; and, optionally, removing residual amounts of the aqueous slurry, finely-divided charcoal, liquid portion, and/or contacted contamination from the tongue, as well as generally from the oral cavity of the patient. For the disclosed method, the aqueous slurry used may be formed from the finely-divided charcoal and liquid portion prior to contacting the area of the tongue surface with the slurry, or after separately contacting the area of the tongue surface with the finely-divided charcoal and liquid portion.

In a related embodiment, the present invention is directed to a method for cleaning the throat of a patient to at least reduce contamination thereof. The disclosed, representative method therefor comprises the same basic steps as the above-described, representative method for cleaning the tongue of a patient, except that areas of the throat, rather than of the tongue, in need thereof are contacted with a disclosed aqueous slurry.

Another embodiment of the present invention is directed to yet another aspect thereof, namely, a kit that is useful for cleaning the tongue and/or throat of a patient to reduce contamination thereof, in providing components that can be readily combined and used for that purpose. More specifically, a representative, disclosed kit comprises: a contained quantity of a disclosed aqueous slurry, or a contained quantity of finely-divided charcoal and, separate therefrom, a contained quantity of the liquid portion, or of the components of the liquid portion of the slurry; optionally, a mixing device adapted to mix the finely-divided charcoal and the liquid portion to form the aqueous slurry; optionally, where the contained quantity of finely-divided charcoal and the contained quantity of the liquid portion, or of the components of the liquid portion, are provided separately, an empty container adapted to provide a reservoir for combining and mixing the quantities of the liquid portion, or components thereof, and of the finely-divided charcoal in desired ratios; optionally, a first contacting device adapted to effect contact of an area of the tongue and/or throat surface with the aqueous slurry and; optionally, a second contacting device adapted to agitatively and frictionally contact the area of the tongue surface with the aqueous slurry; optionally, a removal device adapted to remove the contacted contamination and used aqueous slurry from the area of the tongue surface; and, optionally, a device and/or rinsing agent adapted to remove residual aqueous slurry, components of the liquid portion, finely-divided charcoal and/or contacted contamination from the tongue, throat and other areas of the oral cavity of the patient.

These and other aspects of the present invention will be evident upon reference to the following detailed description of the invention.

DETAILED DESCRIPTION OF THE INVENTION

As mentioned above, the present invention, in one aspect, is directed to aqueous slurries useful for cleaning the tongue and/or throat of a patient to reduce contamination thereof. As used herein, the term "contamination" or "contaminant" generally refers to any unwanted matter present on the surface of the tongue and/or throat of a patient. The matter may or may not be strongly adherent thereto, and may or may not penetrate the surface. Examples of such matter include, but are not limited to, pathogens and microorganisms, such as parasites, bacteria, plaque, viruses, fungi, yeasts, molds and slimes; excreted products of at least some of the same; food debris; food and chemical stains; various products of food decay; and mixtures comprising the aforementioned matter and naturally secreted substances, such as mucous and chemical salts, including calcium carbonate and phosphate. One example of such a mixture is tartar, or calculus. Some of the above-mentioned contaminants are discussed in more detail in the inventor's U.S. patent application Ser. No. 10/223,060, incorporated herein by reference in its entirety.

The disclosed aqueous slurries may be used by an individual human (hereinafter, "individual" or "patient") without the assistance of another for personal oral hygiene purposes: or may be used by an individual on another warm-blooded animal, including an individual (hereinafter, a "subject") to clean the tongue and throat thereof.

As used herein, the phrase "to clean" refers, as one example, to removing or reducing, or causing the removal or reduction of, contamination present on the surface of the tongue and/or throat of a patient. The phrase, as another example, also refers to arresting or inhibiting the growth and/or reproduction of pathogens present thereon, and, as yet another example, also refers to neutralizing, or otherwise chemically altering, contamination present thereon in the sense of eliminating or reducing the ability of the contamination to cause harm, damage, or injury to the patient, or otherwise create an unwanted or disadvantageous condition for the patient.

In one embodiment, the disclosed aqueous slurry is formed by combining finely-divided charcoal and a liquid portion, where the liquid portion comprises a biocide. As used herein, the expression "finely-divided charcoal" also refers to powdered charcoal, finely-divided or powdered carbon, or activated charcoal—all of which are hereinafter referred to by the term "charcoal." As is known to those skilled in the art, charcoal is typically black in color and derived from carbonaceous materials such as wood, peat and coconut shells to yield an odorless, tasteless form of carbon that is safe for consumption by humans and other mammals.

Uses include neutralizing drugs and poisons; providing intestinal gas relief; preventing intestinal infections; purifying air, water, foodstuffs, chemicals and pharmaceuticals; and cleaning surfaces, including tooth surfaces. Activated charcoal is an amorphous form of carbon, characterized by high adsorptivity for many gases, vapors and colloidal solids. It is activated by heating to 800–900° C. with steam or carbon dioxide. This results in a porous internal structure (honeycomb-like). In one embodiment of the present invention directed to an aqueous slurry, the finely-divided charcoal is activated charcoal powder.

Charcoal products are readily commercially available. Some examples of products that are particularly suitable for the present invention are the charcoal products manufactured and sold by Norit Americas Inc. (Atlanta, Ga.) and designated as Norit®A Supra, Norit®B Supra, and Norit®E Supra. The latter products comprise carbon particles, 97% (by weight) of which are less than 150 microns in diameter. Various sizes of carbon particles can be used. Generally desirable, are particle sizes that allow the carbon particles to become suspended in the liquid portion of the slurry, and that allow the carbon particles to be mechanically or fluidly transported to and away from all tongue and throat surfaces, including those not readily accessible in general. For the aqueous slurries disclosed herein, the ratio of the finely-divided charcoal to the liquid portion thereof may vary and, in one embodiment, ranges from about 1:5 to about 1:1 by weight.

Also, as used herein, the term "biocide" refers to a substance that kills, or inhibits the growth or reproduction of, at least some pathogens and/or microorganisms, examples of which are listed above. As noted, disclosed aqueous slurries comprise a liquid portion, that, in turn, comprises water and the biocide. The biocide may be soluble or insoluble in water. Where it is insoluble, the biocide may be dispersed in the water as an emulsion or dispersion by methods known to those skilled in the art.

In a related, more specific embodiment, the liquid portion of the aqueous slurry comprises a biocide selected from chlorine dioxide, cetyl pyridinium (CPC), zinc chloride, alcohol, hydrogen peroxide, or a mixture thereof. All of these biocides are commercially available. CPC is a bacteriostatic compound that, more specifically, is a quaternary ammonium compound having antimicrobial activity against a number of bacteria found in the oral cavity of a patient. It is a component of a number of commercially-available mouthrinses. Chlorine dioxide is a strong oxidizing agent that is an effective biocide, even at low concentrations. Triclosan is a chlorophenol that is highly bacteriostatic and used in commercial products to, for example, stop bad breath. Zinc chloride can inhibit the reproduction of bacterial cells is also found in some commercial products used for oral hygiene.

In another related embodiment, the biocide is selected from alcohol, hydrogen peroxide, or a mixture thereof; and in yet another related embodiment, the biocide is alcohol. Typically, where the biocide is alcohol, the liquid portion is a miscible mixture of water and alcohol. Such mixtures, of which "rubbing alcohol" is one example, are either commercially available, or readily prepared from water and various alcohols, as would be appreciated by one skilled in the art. A few examples of alcohols that can be used are methanol, ethanol and propanol, including isopropyl alcohol. Various concentrations of alcohol in water may be used. In a related, more specific embodiment, the concentration of the alcohol in the liquid portion ranges from about 25% to about 70%, by volume.

In a further, more particular related embodiment, the alcohol is provided by a commercially available mouthrinse, that, in a yet more particular related embodiment, is selected from Listerine® (Warner-Lambert Consumer Healthcare, Morris Plains, N.J.), Scope® (Proctor & Gamble, Cincinnati, Ohio), Plax® (Pfizer, Inc., New York, N.Y.), Act® (Johnson & Johnson, New Brunswick, N.J.) and Cepacol® (J.B. Williams Company, Inc., Glen Rock, N.J.). As used herein, the term "mouthrinse" is synonomous with the term "mouthwash." For certain related embodiments of the aqueous slurry, a commercially available mouthrinse, such as one of those listed above (typically aqueous), is combined and mixed with a quantity of charcoal to form the aqueous slurry.

Various relative amounts of mouthrinse and finely-divided charcoal may be used. Also, the mouthrinse may be used in preparing an aqueous slurry when in a concentrated form, as purchased off the shelf, or after being diluted with water.

The present invention, in another related embodiment, is directed to an aqueous slurry comprising a liquid portion and finely-divided charcoal, wherein the liquid portion comprises water and a biocide provided by hydrogen peroxide. Aqueous solutions of hydrogen peroxide are prepared by methods well known in the art and are used for bleaching, oxidizing, deodorizing, and disinfecting. When the concentration of the hydrogen peroxide in the aqueous solution is at least about 3% by weight, the solution is used medicinally as a disinfectant, for example, to cleanse wounds. Such solutions are readily available as a commercial product. In yet another related embodiment, the biocide is a mixture of alcohol and hydrogen peroxide.

In another aspect, the present invention is directed to a method for cleaning the tongue of a patient to at least reduce the contamination thereof. A representative method comprises: contacting an area of the tongue surface in need thereof with a disclosed aqueous slurry so as to contact contamination present thereon for a period of time; removing at least a portion of the contacted contamination and used aqueous slurry from the area of the tongue surface; optionally, repeating the contacting and removing steps so as to effect a desired degree of cleaning; and, optionally, removing residual amounts of the aqueous slurry, finely-divided charcoal, liquid portion, and/or contacted contamination from the tongue, as well as generally from the oral cavity of the patient. For the disclosed method, the aqueous slurry used may be formed from the finely-divided charcoal and liquid portion prior to contacting the area of the tongue surface with the slurry, or after separately contacting the area of the tongue surface with the finely-divided charcoal and liquid portion.

In related embodiments, the area of the tongue surface is contacted with a disclosed aqueous slurry in an agitative and/or frictional fashion; and using a length of floss, a brush, a pick, a cotton-tipped pick, a cotton swab, a finger, the upper teeth of the patient, a tongue scraper, or a combination thereof. For example, a quantity of a disclosed aqueous slurry is first applied to the area of the tongue surface. In one embodiment, this is accomplished by introducing a desired quantity of aqueous slurry into the oral cavity and swishing it therearound. In a specific, related embodiment, the desired quantity of aqueous slurry is introduced into the oral cavity by ejecting it thereinto using a spray or squeeze bottle. Then, for example, the area of the tongue surface may be rubbed or scraped for a period of time using at least one of the above-listed instruments. As more specific examples, the tongue surface, having a quantity of aqueous slurry applied thereto, may be rubbed with a cotton swab, brushed with a toothbrush, or scraped by drawing back and forth across it a length of floss, the upper teeth, or a tongue scraper. A number of tongue scrapers are commercially available.

In other related embodiments, application of a desired quantity of a disclosed aqueous slurry to the area of the tongue surface is accomplished by using an application means, such as a finger, a brush, a cotton-tipped pick, or a cotton swab, where a quantity of the slurry is transferred to the application means and then transferred therefrom to the tongue. This can be repeated until a total desired quantity is transferred to the tongue. For example, a toothbrush or cotton swab can be dipped into a container of aqueous slurry and then brushed or rubbed against the tongue. This can be done repeatedly.

For the above-disclosed method, the aqueous slurry is typically formed prior to being introduced into the oral cavity. However, this need not be the case. The slurry can be formed in the oral cavity. For example, as disclosed in one embodiment, a quantity of finely-divided charcoal may be introduced into the oral cavity using, for example, a spoon; then a quantity of the liquid portion can be introduced into the oral cavity using, for example, methods described above. The aqueous slurry can then by formed by swishing the liquid portion about the mouth to combine the same with the finely-divided charcoal therein.

In another related embodiment, removing at least a portion of the contacted contamination and used aqueous slurry from the area of the tongue surface is accomplished by brushing, scraping, rubbing, or by using a combination thereof. At least one instrument is used therefor and includes those described above for agitative and/or frictional contact. However, the use thereof for a removal step would typically differ from the use thereof for a contacting step. For example, for a removal step, brushing would typically be carried out in one direction, that being away from the back and toward the front of the tongue, as opposed to using a back and forth or circular motion. Also, in a particular embodiment, the at least one instrument used for the brushing, scraping, rubbing, or combination thereof, has applied to at least a portion of its surface to be placed into contact with the area of the tongue surface, a quantity of the liquid portion of the aqueous slurry, the aqueous slurry, another liquid, toothpaste, or the finely-divided charcoal.

In anther specific, related embodiment, the removal of at least a portion of the contacted contamination and used aqueous slurry from the area of the tongue surface is carried out by rinsing with a liquid, by aspirating with a vacuum, or by using a combination thereof. The optional removal of residual amounts of the aqueous slurry, finely-divided charcoal, liquid portion, and/or contacted contamination from the tongue, as well as generally from the oral cavity of the patient, in one specific embodiment, is accomplished by rinsing, brushing, or using a combination thereof.

In another, but related aspect, the present invention is directed to a method for cleaning the throat of a patient to at least reduce the contamination thereof. Paralleling the disclosed, representative method for cleaning the tongue of a patient, a representative method for cleaning the throat comprises: contacting an area of the throat surface in need thereof with a disclosed aqueous slurry so as to contact contamination present thereon for a period of time; removing at least a portion of the contacted contamination and used aqueous slurry from the area of the tongue surface; optionally, repeating the contacting and removing steps so as to effect a desired degree of cleaning; and, optionally, removing residual amounts of the aqueous slurry, finely-divided charcoal, liquid portion, and/or contacted contamination from the throat, as well as generally from the oral cavity of the patient. For the disclosed method, the aqueous slurry used may be formed from the finely-divided charcoal and liquid portion prior to contacting the area of the throat surface with the slurry, or after separately contacting the area of the throat surface with the finely-divided charcoal and liquid portion.

In one related embodiment, the area of the throat surface is contacted with a disclosed aqueous slurry by introducing a desired quantity of the aqueous slurry into the oral cavity and gargling therewith. In another related embodiment, the liquid portion and finely-divided charcoal components of a disclosed aqueous slurry can be introduced into the oral cavity separately and mixed therein to form the slurry by, for example, using facial muscles and the tongue to swish the components therearound. Then, the area of the throat surface is contacted as before with the aqueous slurry by gargling. In yet another related embodiment, the area of the throat surface is contacted with a disclosed aqueous slurry by spraying a desired quantity of the same directly onto the area.

Typically, removing contacted contamination and used aqueous slurry from the area of the throat surface is accomplished by gargling or direct spraying onto the surface with additional aqueous slurry or some other liquid, such as a commercially available mouthrinse or saltwater. A similar technique may be used to remove residual amounts of used aqueous slurry, finely-divided charcoal, liquid portion and/or contacted contamination from the throat, as well as generally from the oral cavity.

Finally, in another aspect, the present invention is directed to a kit that is useful for cleaning the tongue and/or throat of a patient to reduce contamination thereof. As noted, the disclosed kit provides components that can be readily combined and used for that purpose. More specifically, a representative, disclosed kit comprises: a contained quantity of a disclosed aqueous slurry, or a contained quantity of finely-divided charcoal and, separate therefrom, a contained quantity of the liquid portion, or of the components of the liquid portion of the slurry; optionally, a mixing device adapted to mix the finely-divided charcoal and the liquid portion to form the aqueous slurry; optionally, where the contained quantity of finely-divided charcoal and the contained quantity of the liquid portion, or of the components of the liquid portion, are provided separately, an empty container adapted to provide a reservoir for combining and mixing the quantities of the liquid portion, or components thereof, and of the finely-divided charcoal in desired ratios; optionally, a first contacting device adapted to effect contact of an area of the tongue and/or throat surface with the aqueous slurry and; optionally, a second contacting device adapted to agitatively and frictionally contact the area of the tongue surface with the aqueous slurry; optionally, a removal device adapted to remove the contacted contamination and used aqueous slurry from the area of the tongue surface; and, optionally, a device and/or rinsing agent adapted to remove residual aqueous slurry, components of the liquid portion, finely-divided charcoal and/or contacted contamination from the tongue, throat and other areas of the oral cavity of the patient.

A contained quantity of aqueous slurry or a component thereof refers to a quantity of the same that is in a sealed container. Examples of the latter include a sealed bottle, vial or packet. Where components are provided, the liquid portion may be provided as a mixture of water and biocide, or may be provided as separate components to be mixed. Also, where components are provided, each component may be pre-measured in one or more containers to allow for ready combination of quantities in one or more desired ratios. Or, a graduated empty container may be provided for mixing components in various desired ratios. Devices and rinsing agents, optionally provided in the kit for contacting areas of the tongue and/or throat with the aqueous slurry provided by the kit, and/or removing material from the oral cavity, include those described previously herein for the disclosed methods of the present invention.

All of the U.S. patents, U.S. patent application publications, U.S. patent applications, foreign patents, foreign-patent applications and non-patent publications listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for cleaning the tongue of a patient to reduce contamination thereof, comprising:
   (a) contacting an area of the tongue surface in need thereof with the aqueous slurry so as to contact contamination thereon, the aqueous slurry comprising finely-divided charcoal, water and a biocide, wherein the water and an alcohol biocide provide, and are components of, a liquid portion of the aqueous slurry, and the aqueous slurry is formed by mixing the finely-divided charcoal with the liquid portion;

(b) removing at least a portion of the contacted contamination and used aqueous slurry from the area of the tongue surface;

(c) optionally, repeating (a) and (b) until a desired degree of cleaning is accomplished; and (d) optionally, removing residual amounts of the aqueous slurry, finely-divided charcoal, liquid portion, and/or contacted contamination from the tongue, as well as from the oral cavity of the patient, wherein the aqueous slurry is formed prior to contacting the area of the tongue surface with the aqueous slurry, or during (a).

2. The method of claim 1 wherein (a) comprises agitative and/or frictional contact of the area of the tongue surface with the aqueous slurry.

3. The method of claim 2 wherein the agitative and/or frictional contact is accomplished by using a length of floss, a brush, a pick, a cotton-tipped pick, a cotton swab, a finger, the upper teeth of the patient, a tongue scraper, or a combination thereof.

4. The method of claim 1 wherein (a) comprises introducing a desired quantity of the aqueous slurry into the oral cavity and swishing the aqueous slurry therearound.

5. The method of claim 4 wherein the desired quantity of the aqueous slurry is introduced into the oral cavity using a spray or squeeze bottle.

6. The method of claim 1 wherein (a) comprises transferring a desired quantity of the aqueous slurry to an applicator means, then bringing the applicator means into contact with the area of the tongue surface so as to transfer the aqueous slurry thereto.

7. The method of claim 6 wherein the applicator means is a finger, a brush, a cotton-tipped pick, or a cotton swab.

8. The method of claim 1 wherein (a) is accomplished by separately introducing the finely-divided charcoal and the liquid portion into the oral cavity so as to transfer at least a portion of the charcoal and the liquid portion to the area of the tongue surface, and mixing the transferred portions on the area of the tongue surface, as well as at other locations in the oral cavity.

9. The method of claim 1 wherein (b) is accomplished by brushing, scraping, rubbing, or by using a combination thereof.

10. The method of claim 9 wherein the brushing, scraping, rubbing or combination thereof is carried out using at least one instrument, suitable therefor, wherein the at least one instrument has applied to at least a portion of its surface to be placed into contact with the area of the tongue surface, a quantity of the liquid portion of the aqueous slurry, the aqueous slurry, another liquid, toothpaste, or the finely-divided charcoal.

11. The method of claim 9 wherein the scraping, rubbing or combination thereof is accomplished using a pick, a cotton-tipped pick, a cotton swab, a length of floss, a finger, a tongue scraper, the upper teeth of the patient, or by using a combination thereof.

12. The method of claim 1 wherein (b) is accomplished by rinsing with a liquid, by aspirating with a vacuum, or by a combination thereof.

13. The method of claim 1 wherein step (d) is accomplished by rinsing, brushing, or using a combination thereof.

14. A method for cleaning the throat of a patient to reduce contamination thereof, comprising the steps of:

(a) contacting an area of the throat surface in need thereof with an aqueous slurry so as to contact contamination thereon, the aqueous slurry comprising finely-divided charcoal, water and an alcohol biocide, wherein the water and biocide provide, and are components of, a liquid portion of the aqueous slurry, and the aqueous slurry is formed by mixing the finely-divided charcoal with the liquid portion;

(b) removing at least a portion of the contacted contamination and used aqueous slurry from the area of the throat surface;

(c) optionally, repeating steps (a) and (b) until a desired degree of cleaning is accomplished; and (d) optionally, removing residual amounts of the aqueous slurry, finely-divided charcoal, liquid portion, and/or contacted contamination from the throat, as well as generally from the oral cavity of the patient, wherein the aqueous slurry is formed prior to contacting the area of the tongue surface with the aqueous slurry, or during (a).

15. The method of claim 14 wherein (a) is accomplished by introducing a desired quantity of the aqueous slurry into the oral cavity and gargling therewith.

16. The method of claim 14 wherein (a) comprises spraying the aqueous slurry directly onto the area of the throat surface.

17. A kit useful for cleaning the tongue and/or throat of a patient to reduce contamination thereof, comprising:

a contained quantity of an aqueous slurry, the aqueous slurry comprising finely-divided charcoal, water and an alcohol biocide, wherein the water and biocide provide, and are components of, a liquid portion of the aqueous slurry, and the aqueous slurry is formed by mixing the finely-divided charcoal with the liquid portion or a contained quantity of finely-divided charcoal and, separate therefrom, a contained quantity of the liquid portion, or of the components of the liquid portion;

a mixing device adapted to mix the finely-divided charcoal and the liquid portion to form the aqueous slurry;

optionally, where there is provided separately the contained quantity of finely-divided charcoal and the contained quantity of the liquid portion, or of the components of the liquid portion, an empty container adapted to provide a reservoir for combining and mixing the quantities of the liquid portion and of the finely-divided charcoal, or of the components of the liquid portion and of the finely-divided charcoal;

optionally, a first contacting device adapted to effect contact of an area of the tongue and/or throat surface with the aqueous slurry;

optionally, a second contacting device adapted to agitatively and frictionally contact the area of the tongue surface with the aqueous slurry;

optionally, a removal device adapted to remove the contacted contamination and used aqueous slurry from the area of the tongue surface; and optionally, a device and/or rinsing agent adapted to remove residual aqueous slurry, components of the liquid portion, finely-divided charcoal and/or contacted contamination from the tongue, throat and other areas of the oral cavity of the patient.

18. The kit of claim 17 wherein the components of the liquid portion are selected from water, alcohol and hydrogen peroxide, or a mixture thereof.

19. The kit of claim 17 wherein the first contacting device is selected from a brush, a cotton-tipped pick or a cotton swab; and the second contacting device is a pick, and a tongue scraper.

* * * * *

UNITED STATES PATENT AND TRADEMARK OFFICE
CERTIFICATE OF CORRECTION

PATENT NO. : 6,861,049 B2
DATED : March 1, 2005
INVENTOR(S) : Douglas B. Harwood It is certified that error appears in the above-identified patent and that said Letters Patent is hereby corrected as shown below:

Column 8,
Line 67, "water and a biocide" should read as -- water and an alcohol biocide --.

Column 10,
Line 32, "liquid portion or a" should read as -- liquid portion; or a --.

Signed and Sealed this

Thirtieth Day of August, 2005

JON W. DUDAS
*Director of the United States Patent and Trademark Office*